United States Patent [19]

Hjerten

[11] Patent Number: 5,073,239
[45] Date of Patent: Dec. 17, 1991

[54] FLUID INTRODUCTION INTO A CAPILLARY BY ELECTROENDOSMOSIS

[75] Inventor: Stellan Hjerten, Upsala, Sweden

[73] Assignee: Bio-Rad Laboratories, Inc., Hercules, Calif.

[21] Appl. No.: 469,640

[22] Filed: Jan. 24, 1990

[51] Int. Cl.$^5$ .................... G01N 27/26; B01D 57/02
[52] U.S. Cl. ............................ 204/180.1; 204/299 R
[58] Field of Search ............. 204/299 R, 180.1, 183.3

[56] References Cited

PUBLICATIONS

Everaerts, F. M. et al. "Simple Sampling Device for Capillary Isotachophoresis and Capillary Zone Electrophoresis" Journal of Chromatography 452 (1988) 615–622.

Bocek, P. et al, "Electric Sample Splitter for Capillary Zone Electrophoresis Journal of Chromatography", 320 (1985) 159–165.

*Primary Examiner*—John Niebling
*Assistant Examiner*—John S. Starsiak, Jr.
*Attorney, Agent, or Firm*—Townsend and Townsend

[57] ABSTRACT

Bulk fluid movement in a capillary column is achieved by creating electroendosmotic flow in a fluid passage outside the column, the fluid passage being joined to the column in a manner which causes the electroendosmotic flow to generate bulk flow in the column and yet permits an electric potential to be applied across the fluid passage and not the column. Small volume bulk fluid movement induced in this manner may be used to load sample into the column, whereas a larger induced volume may be used for flushing the column between runs. To alternate the bulk fluid movement with electrophoretic separations in the column, the column is arranged such that an electric potential can also be applied across the column without extending to the electroendosmotic fluid passage.

21 Claims, 2 Drawing Sheets

FLUID INTRODUCTION INTO A CAPILLARY BY ELECTROENDOSMOSIS

This invention lies in the field of capillary separation processes, and also relates to electroendosmotic flow. In particular, this invention addresses a method for moving fluids in bulk flow either into or through a capillary separatory column.

BACKGROUND OF THE INVENTION

Capillaries are useful in separatory processes of various kinds. Examples of such processes are various forms of electrophoresis, including free-zone or open-tube electrophoresis, isotachophoresis and isoelectric focusing, both with and without electroendosmotic flow. Due to their small internal volume, capillaries can effectively separate extremely small samples, and can do so at high speed. Capillaries are of particular interest in electrophoretic separations since the narrow bore of a capillary promotes rapid heat dissipation outward, which permits the use of high voltages. This provides high speed and efficiency, rendering capillaries particularly useful for analyzing samples of biological interest, particularly mixtures of small peptides, proteins and nucleic acids.

One of the problems in capillary electrophoresis is the flushing of the capillary with buffer or wash solution in between separations. This is generally achieved by pressure differential techniques, which require external apparatus such as a pump or a vacuum line. Such apparatus presents problems in designing systems for the automated analysis of a series of samples, and is generally awkward in terms of its integration with the other components associated with the system. Problems also arise from the limited extent to which one can control the pressure differential and its duration.

A further problem is the loading of the sample, i.e., its placement inside the end of the capillary in preparation for the separation. At present, this is commonly achieved by electrophoretic, electroendosmotic or pressure differential techniques.

In electrophoretic loading, a high voltage is used over a short period of time to transfer the sample from a sample reservoir into the capillary itself. The goal is to move small amounts of all species in the sample a short distance into the capillary. Once this is done, the sample reservoir is replaced with an appropriate buffer solution to permit one to proceed with electrophoretic separation of the loaded species.

In electroendosmotic loading, the fluid is moved primarily by bulk flow into the capillary as the result of an electroendosmotic effect in the capillary. What actually occurs in electroendosmotic loading is a combination of electrophoresis and electroendosmosis, with electroendosmosis having the predominating effect. The disadvantage of electroendosmosis is that it varies from one experiment to the next, causing difficulties in the reproducibility of the sample volume. One can eliminate electroendosmosis as a driving force by applying an appropriate coating to the inside of the capillary. This will leave electrophoresis as the sole driving force.

Electrophoretic loading, however, has its own disadvantages. These arise from the differentials which necessarily exist among the various species in the sample in terms of their response to the electric potential. These differentials affect the distance which the species travel into the capillary during sample loading and thus the amounts of each species entering the capillary. Slowly migrating substances will thus migrate a shorter distance into the tube than will the faster migrating substances. Depending on the loading conditions, therefore, the composition of the applied sample may differ from that of the original sample.

Electrophoretic and electroendosmotic loading both have the further drawback that the current will cause an increase in temperature in the capillary. This fact gives rise to an expansion of the liquid in the capillary, which may cause part of the sample to be displaced backwards out of the capillary in an irreproducible way. This in turn may mean that the amount of sample introduced will vary from one experiment to the next.

Other variables in electrophoresis such as fluctuations in current strength may also enter into consideration. The significance and importance of these variables will vary from one system to the next.

In hydraulic loading, sample introduction is achieved in the same manner as the column flushing referred to above, i.e., either by applying a partial vacuum to the outlet end of the capillary or a positive pressure to the inlet end. The limited extent to which one can control the pressure differential and its duration present even more of a problem here, since they affect the volume of the sample introduced.

SUMMARY OF THE INVENTION

A method and apparatus have now been devised whereby bulk liquid flow is achieved in a separation capillary (hereinafter referred to as the "column") by an electroendosmotic flow created outside the column. In particular, the column is placed in fluid communication with a fluid passage in which an electroendosmotic effect can be generated separately from the capillary. The column and the fluid passage are connected in such a manner that flow through the fluid passage forces flow through the column, despite the ability to impose an electric potential across the fluid passage to the exclusion of the column.

In preferred embodiments, the fluid passage is a capillary itself, and the electric potential used to induce the electroendosmotic driving force is achieved by a pair of electrodes both positioned at the same end of the column with the electroendosmosis capillary in between.

This discovery is of particular interest in capillary electrophoresis systems, and is applicable to small volume introductions into the tube for purposes such as loading sample, as well as large volume transfers into or through the tube for purposes such as flushing the tube with buffer.

DETAILED DESCRIPTION OF THE INVENTION AND PREFERRED EMBODIMENTS

Figure 1:
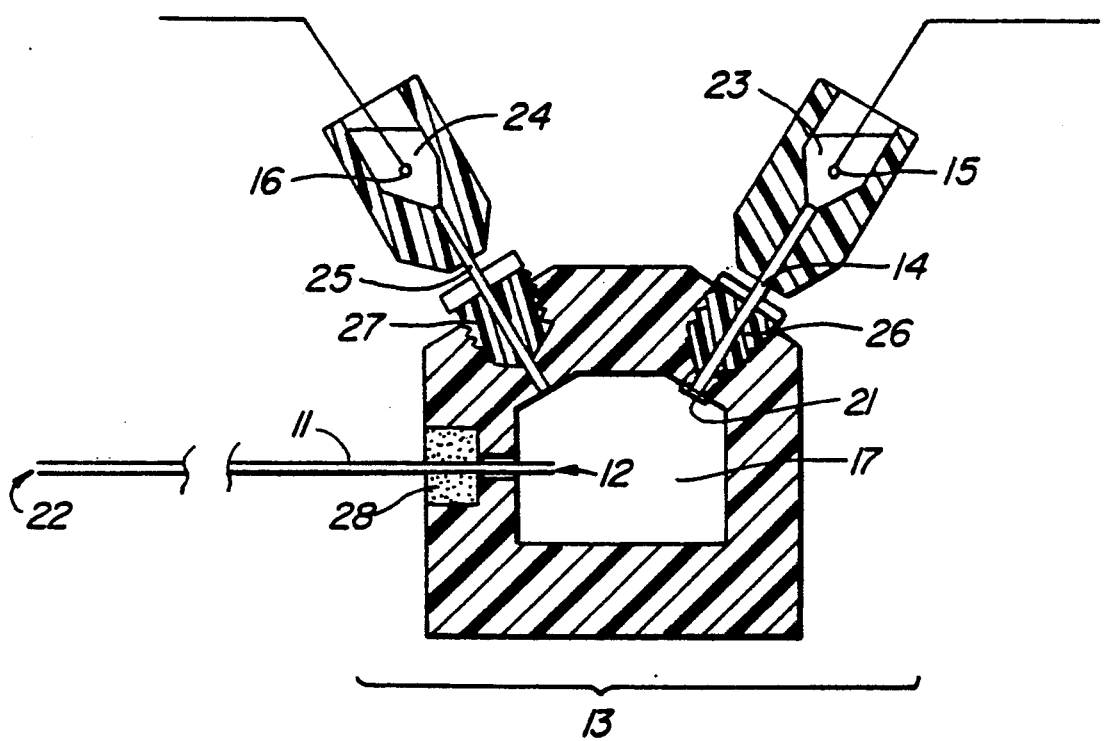
FIG. 1 is a cutaway view depicting apparatus for creating electroendosmotic flow external to a capillary separation column in a manner which will force liquid to flow into the column.

FIG. 1 depicts one example of an arrangement by which liquid flow can be induced in a column by an electroendosmotic force external to the column. The apparatus shown in this figure can conveniently be termed an "electroendosmotic pump." What is shown in this figure is a column 11 one end 12 of which is adjoined to the electroendosmotic pump 13. Components of the electroendosmotic pump 13 include the fluid passage 14 in which the electroendosmotic driving force is created, a pair of electrodes 15, 16 positioned to span a fluid path which includes the fluid passage 14 but not the column 11, and an enclosed chamber 17 joining the fluid passage 14 with the column in such a manner that fluid flow occurring in the fluid passage 14 is transmitted to the column.

The fluid passage 14 may be of any configuration in which bulk flow will occur under an electroendosmotic driving force, i.e., one which will either draw liquid from or expel liquid into the enclosed chamber 17. Cross sections and internal volumes may vary, but the preferred configuration is that of a capillary. The size of the capillary in terms of its diameter and length is not critical and can vary widely. The flow rate generated by the electroendosmotic driving force is independent of the capillary length. As for the diameter, selection of the optimal diameter may depend on the size of the column or on whether the electroendosmotic effect is intended for sample introduction, full column flushing or both. In most cases, capillaries having inner diameters of about 0.02 mm to about 0.5 mm microns will be used, preferably those with inner diameters of about 0.5mm to about 3 mm. For convenience throughout the remainder of this specification, the term "pump capillary" will designate this capillary.

The pump capillary 14 and its contents will be of materials susceptible to producing electroendosmotic flow under the influence of an electric potential. Maintenance and control of the electroendosmotic effect may be related to the material from which the wall of the capillary itself is made. This may for example be modified or enhanced by the use of a coating applied to the capillary wall. Such coating materials are known among those skilled in the art. Selection of an appropriate medium inside the capillary space will also ensure that electroendosmotic takes place. The effect can be achieved with charged particles, both connected with each other and non-connected, preferably connected, as well as gels and liquid solutions. Gels are preferred, with agar gels particularly preferred.

In preferred embodiments of the invention, the pump capillary 14 will be closed off at the end which is in fluid communication with the column by a membrane 21 which permits passage of the electric current but not a hydrodynamic flow. The membrane and/or the capillary filling (a gel, for example) should be selected and affixed to the capillary in such a way that they will not be forced backwards by the electroendosmotic flow. This is of particular importance in achieving reproducibility. A variety of such membranes are commercially available and known among those skilled in the art. Examples are dialysis membranes and cation and anion membranes. The purpose of this membrane is to prevent gel in the pump capillary 14 from moving into the chamber 17. If the membrane is strongly charged, it will itself generate a sufficiently high electroendosmotic flow to serve the purposes of the invention without the inclusion of a gel in the capillary. On the other hand, the need for the membrane can be eliminated by the use of a charged gel which is covalently linked to the inside of the capillary 14.

The enclosed chamber 17 is sealed to transmit the fluid mobilization in the pump capillary 14 to the column. Thus, when the polarity of the electrodes 15, 16 is such that fluid is drawn from the chamber 17 through the membrane 21 into the pump capillary 14, a corresponding volume of fluid will be drawn from the column 11 into the chamber 17. The fluid remaining in the column moves a corresponding distance to the right (according to the view shown in the drawing), and if this occurs while the opposite end 22 of the column is immersed in fluid, an equal volume of that fluid will enter the column at that end. Conversely, when the polarity of the electrodes is reversed, fluid is expelled from the pump capillary 14 through the membrane 21 into the chamber 17, and a corresponding volume of fluid is forced from the chamber 17 into the column 11. The amount of fluid transferred is controlled by the length of time the electric potential is maintained as well as the magnitude of the potential, the charge on the capillary wall, the charge on the gel or charged particles in the capillary, or a combination of these. The potential may thus be used to cause any volume of fluid to enter the column 11, ranging from a sample-size volume to a volume exceeding the entire internal volume of the capillary. Appropriate selection of the duration and magnitude of the potential are readily determinable by either routine experimentation or by calculation. For column flushing, for example, for a capillary having dimensions within the ranges given above, typical values for the potential may lie within the ranges of about 100 to about 1000 volts for about 0.2 to about 2.0 minutes. For sample loading in similar systems, typical values may lie within the ranges of about 20 to about 200 volts for about 0.05 to about 0.5 minutes.

It will be noted from the drawing that in the embodiment shown, the two electrodes 15, 16 are each positioned in open buffer reservoirs 23, 24, respectively. This permits ions and fluid to move electrophoretically into and out of each reservoir as needed to permit bulk flow through the column 11. It also permits gas bubbles generated at the electrodes to escape.

There must be sufficient sealing in the chamber 17, however, that bulk flow in the pump capillary 14 is transmitted to the column. This is achieved by using a chamber whose only openings, other than the column itself, are those leading to the electrodes. In addition, the opening to the electrode 16 which is counter to the electrode 15 associated with the pump capillary must be one which offers greater resistance to flow than the column itself such that the transmitted flow arising from the electroendosmotic pump effect will occur in the column only.

In the embodiment shown in the drawing, this is achieved by the use of an additional capillary 25 as the connection between the counter electrode buffer reservoir 24 and the chamber 17. A higher flow resistance in this capillary (referred to for convenience herein as the "counter electrode capillary") than in the column may be achieved by the placement of a nonionic gel in the capillary.

To assure that the flow from the electroendosmotic pump effect is confined to the column, the counter electrode capillary is preferably one which is not susceptible to an electroendosmotic effect of its own while under the influence of the electric potential creating the electroendosmotic effect in the pump capillary. This may be achieved in a variety of ways known to those skilled in the art. For embodiments where flow resistance in the counter electrode capillary is achieved by some method other than a gel, avoidance of the electroendosmotic effect may be achieved by using a capillary tube of a material which does not give rise to the electroendosmotic effect, or one which is coated with a material which suppresses the electroendosmotic effect. Descriptions of such coatings are found in Hjertén, S., U.S. Pat. No. 4,680,201, issued July 14, 1987, incorporated herein by reference. A preferred coating for a glass capillary is linear polyacrylamide secured to the glass wall by an appropriate coupling agent such as γ-methacryloxypropyltrimethoxysilane.

In preferred systems, the counter electrode capillary is filled with a gel appropriately selected to avoid an electroendosmotic effect. The preferred gel is a polyacrylamide gel. An appropriate silane coupling agent may also be included to securely bond the gel to the capillary walls.

Further features which seal the enclosed chamber 17 are threaded plugs 26, 27 for securing the pump and counter electrode capillaries, respectively, into appropriately positioned ports in the chamber in liquid-tight manner, and a liquid-tight seal 28 of an appropriate material such as silicone rubber surrounding the column 11 at its point of entry.

Figure 2:
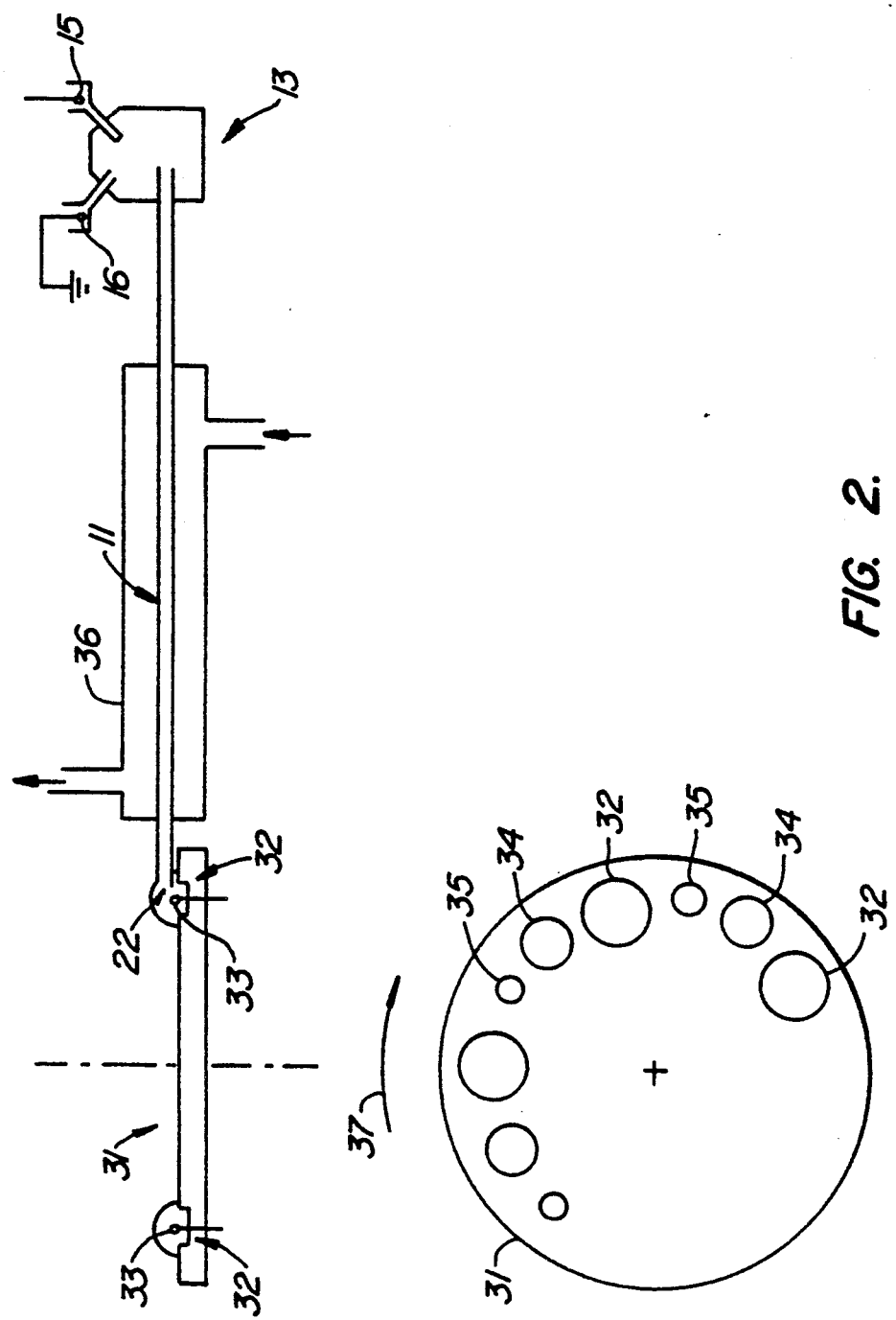
FIG. 2 is a diagram of a capillary electrophoresis system incorporating the apparatus of FIG. 1.

FIG. 2 shows the electroendosmotic pump of FIG. 1 incorporated into an entire capillary electrophoresis system. Here the electroendosmotic pump 13 is positioned at one end of the column 11 while a carousel 31 containing wells 32 each accommodating a buffer solution and an electrode 33 is placed at the other end of the column 11. The plan view of the carousel included in the drawing indicates that the carousel also includes wells 34 for a wash solution and further wells 35 for sample, in repeating sequence. The carousel surface is of a nonwettable material such as Teflon which permits the liquid in the wells to form beads above the carousel surface when the wells are overfilled. To perform each function, i.e., sample loading, separation, and column flushing, the carousel is rotated into position so that the appropriate well is aligned with the open end 22 of the column which extends into the bead, placing the well contents in fluid contact with the column interior. This arrangement avoids the necessity of moving the carousel or the end section of the capillary up and down in order to make and break contact with the contents of each of the wells in succession. When wells and liquid volumes of very small size are used, the carousel may be placed in a laboratory hood or other chamber to maintain an atmosphere saturated with water vapor. This will prevent evaporation from the bead.

FIG. 2 represents but one example of a method of loading the column 11 with sample and placing the open end 22 of the column in contact with a wash solution and an electrode buffer. Other methods and configurations will be readily apparent to those skilled in the art.

The electrodes in this system are arranged in two pairs which have one electrode in common. The first pair consists of the two electrodes associated with the electroendosmotic pump, as described above, i.e., the electrode 15 associated with the pump capillary 14 and the counter electrode 16. The second pair consists of the electrodes 33 in the buffer wells 32 of the carousel (these electrodes are considered individually, since only one is energized at a time) and the counter electrode 16. The latter thus is preferably used for both potentials, i.e., for both the electroendosmotic pump and the separation, and is preferably grounded as indicated in the drawing.

Other optional features of the system are the use of a coated capillary tube as the column 11, and a temperature-controlled jacket 36 surrounding the column.

The coating is one which will prevent electroendosmotic bulk flow in the column, and may be linear polyacrylamide or any other coating effective for this purpose. One is again referred to Hjertén, S., U.S. Pat. No. 4,680,201, referenced above.

The jacket 36 is arranged to allow a heat transfer fluid to pass over the exterior of the column, thereby controlling the temperature of the column. The jacket may also be used to change the column temperature by a controlled preselected temperature differential as an alternative method of achieving bulk fluid movement in the column in an accurately controlled manner. A more detailed description of this technique is found in commonly owned copending U.S. patent application Ser. No. 07/370,368, filed June 22, 1989, incorporated herein by reference. For example, sample loading may be achieved by changing the column temperature in this manner, while flushing the column in between runs may be achieved by the electroendosmotic effect. Other combinations are readily apparent.

The following is one example of how a system such as that depicted in FIG. 2 may be operated.

The carousel 31 is first placed at a position in which a wash solution well 34 is aligned with the column 11. With the carousel in this position, a voltage is applied across the electrodes 15 and 16. A typical value is 500 volts for a period of 0.5 minute. This results in flushing of the column with solution from the well 34. Alternatively, the capillary 11 can be flushed with fresh liquid from the chamber 17 (FIG. 1); the liquid occupying the capillary will then be disposed of in the well 34. The column temperature is equilibrated at a preselected level during this time by a heat transfer liquid flowing through the jacket 36. The carousel is then rotated in the direction of the arrow 37 until the adjacent sample well 35 is in alignment with the column 11. The flowing heat transfer liquid is then replaced by heat transfer liquid at a lower temperature selected to achieved a predetermined contraction of the buffer solution in the column, the contraction being such that a preselected volume of sample is drawn into the column from the sample well 35.

The carousel is then rotated further in the direction of the arrow 37 until the adjacent electrode buffer well 32 is in alignment with the column. With no voltage applied to the pump electrode 15, a high voltage is now applied between the well electrode 33 and the grounded counter electrode 16. This voltage is then switched off after a desired period of time sufficient to obtain a separation of the sample and detection of its components. Detection is achieved in accordance with techniques known in the art, as are all other functions and actions performed by the system and not described in detail above.

The foregoing is offered primarily for purposes of illustration. It will be readily apparent to those skilled in the art that numerous variations, modifications and substitutions beyond those described herein may be made without departing from the spirit and scope of the invention.

What is claimed is:

1. A method for introducing a selected volume of liquid into a capillary tube in a capillary electrophoretic system, said capillary tube filled with an electrophoretic separation medium, said method comprising:

(a) arranging said capillary tube to open into a body of said liquid and to be in fluid communication with a fluid passage filled with a medium, said fluid passage, said medium or both tending to induce electroendosmotic flow in said fluid passage in the presence of an electric potential, said fluid passage arranged such that electroendosmotic flow so induced therein causes bulk flow in said capillary tube; and (b) applying an electric potential across said fluid passage without applying an electric potential across said capillary tube, thereby causing electroendosmotic flow in said fluid passage and bulk flow of said electrophoretic separation medium in said capillary tube, until said selected volume of liquid has entered said capillary tube.

2. A method in accordance with claim 1 in which said capillary tube is defined as a first capillary tube, said fluid passage is defined as a second capillary tube, and step (a) comprises arranging said first and second capillary tubes such that each opens into a common enclosed chamber.

3. A method in accordance with claim 1 in which said capillary tube is defined as a first capillary tube, said fluid passage is defined as a second capillary tube, and step (a) comprises arranging said first and second capillary tubes and a third capillary tube such that each opens into a common enclosed chamber, and such that said second and third capillary tubes also open into separate electrode reservoirs defined as first and second electrode reservoirs, respectively, and step (b) comprises applying an electric potential between said first and second electrode reservoirs.

4. A method in accordance with claim 1 in which:
said capillary tube is defined as a first capillary tube, said fluid passage is defined as a second capillary tube, and step (a) comprises arranging said first and second capillary tubes and a third capillary tube such that each opens into a common enclosed chamber, and such that said second and third capillary tubes also open into separate electrode reservoirs defined as first and second electrode reservoirs, respectively;
said second and third capillary tubes present greater resistance to fluid flow therethrough than said first capillary tube; and
step (b) comprises applying an electric potential between said first and second electrode reservoirs.

5. A method in accordance with claim 1 in which:
said capillary tube is defined as a first capillary tube, said fluid passage is defined as a second capillary tube, and step (a) comprises arranging said first and second capillary tubes and a third capillary tube such that each opens into a common enclosed chamber, said second and third capillary tubes connecting said enclosed chamber with first and second electrode reservoirs, respectively;
said electrophoretic separation medium is a buffer solution, and said third capillary tube is filled with a gel which is not susceptible to electroendosmotic flow therethrough; and
step (b) comprises applying an electric potential between said first and second electrode reservoirs.

6. A method in accordance with claim 1 in which step (a) comprises placing said body of said liquid at the same end of said capillary tube as said fluid passage.

7. A method in accordance with claim 1 in which step (a) comprises placing said body of said liquid and said fluid passage at opposite ends of said capillary tube.

8. A method in accordance with claim 1 in which:
said capillary tube is defined as a first capillary tube, said fluid passage is defined as a second capillary tube, and step (a) comprises arranging said first and second capillary tubes and a third capillary tube such that each opens into a common enclosed chamber, said second and third capillary tubes connecting said enclosed chamber with first and second electrode reservoirs, respectively;
said electrophoretic separation medium is a buffer solution, said second capillary tube is filled with agar gel, and said third capillary tube is filled with acrylamide gel; and
step (b) comprises applying an electric potential between said first and second electrode reservoirs.

9. A method in accordance with claim 8 in which said second capillary tube is separated from said enclosed chamber by an ion-permeable membrane which blocks hydrodynamic flow.

10. Electrophoresis apparatus comprising:
a capillary tube;
a fluid passage filled with a medium, said fluid passage, said medium or both tending to induce electroendosmotic flow in said fluid passage in the presence of an electric potential, said fluid passage arranged such that electroendosmotic flow so induced therein causes bulk flow in said capillary tube;
first electric potential means for applying an electric potential across said fluid passage without applying an electric potential across said capillary tube; and
second electric potential means for applying an electric potential across said capillary tube without applying an electric potential across said fluid passage.

11. Electrophoresis apparatus in accordance with claim 10 in which said capillary tube is defined as a first capillary tube, and said fluid passage is a second capillary tube.

12. Electrophoresis apparatus in accordance with claim 10 further comprising an enclosed chamber; and in which said capillary tube is defined as a first capillary tube, said fluid passage is a second capillary tube, and said first and second capillary tubes both open into said enclosed chamber.

13. Electrophoresis apparatus in accordance with claim 12 in which said second capillary tube is separated from said enclosed chamber by an ion-permeable membrane which blocks hydrodynamic flow.

14. Electrophoresis apparatus in accordance with claim 10 in which said first electric potential means comprises a first pair of electrodes, and said second electric potential means comprises a second pair of electrodes, said first pair of electrodes spanning a fluid path which includes said fluid passage and does not include said capillary tube, and said second pair of electrodes spanning a fluid path which includes said capillary tube and does not include said fluid passage.

15. Electrophoresis apparatus in accordance with claim 14 in which said first pair of electrodes and said second pair of electrodes have one electrode in common.

16. Electrophoresis apparatus in accordance with claim 14 in which said first pair of electrodes are defined as first and second electrodes, and said second pair of electrodes are comprised of said second electrode and a third electrode; said electrophoresis apparatus further comprises an enclosed chamber; said capillary tube is defined as a first capillary tube, and said fluid passage is a second capillary tube positioned between said first electrode and said enclosed chamber; and said apparatus further comprises a third capillary tube positioned between said second electrode and said enclosed chamber.

17. Electrophoresis apparatus in accordance with claim 16 in which said second capillary tube is filled with a first medium, said second capillary tube or said first medium or both selected such that, when an electric potential is imposed across said second capillary tube, electroendosmotic flow is induced therein, and said third capillary tube is filled with a second medium, said third capillary tube and said second medium selected such that substantially no electroendosmotic flow occurs therein when an electric potential is imposed across said third capillary tube.

18. Electrophoresis apparatus in accordance with claim 17 in which said first and second media are gels.

19. Electrophoresis apparatus in accordance with claim 17 in which said first medium is an agar gel and said second medium is an acrylamide gel.

20. Electrophoresis apparatus in accordance with claim 17 in which said second capillary tube is of a material tending to induce said electroendosmotic flow.

21. Electrophoresis apparatus in accordance with claim 17 in which said medium tends to induce said electroendosmotic flow, and said medium is comprised of charged particles.

* * * * *